United States Patent
Honda et al.

(10) Patent No.: US 6,965,429 B2
(45) Date of Patent: Nov. 15, 2005

(54) METHOD OF REVIEWING DETECTED DEFECTS

(75) Inventors: Toshifumi Honda, Yokohama (JP); Yuji Takagi, Kamakura (JP); Hirohito Okuda, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/224,087

(22) Filed: Aug. 19, 2002

(65) Prior Publication Data

US 2003/0058435 A1 Mar. 27, 2003

(30) Foreign Application Priority Data

Sep. 26, 2001 (JP) ....................................... 2001-292790

(51) Int. Cl.[7] .............................................. G01N 21/00
(52) U.S. Cl. .................................... 356/237.1; 356/394
(58) Field of Search ......................... 356/237.1–237.6, 356/394; 250/306, 307, 310, 559.29, 559.31; 382/151

(56) References Cited

U.S. PATENT DOCUMENTS

| | | | | |
|---|---|---|---|---|
| 5,298,963 A | * | 3/1994 | Moriya et al. ................. 356/31 |
| 5,659,172 A | * | 8/1997 | Wagner et al. ............... 250/307 |
| 5,750,990 A | * | 5/1998 | Mizuno et al. .............. 250/307 |
| 5,943,437 A | * | 8/1999 | Sumie et al. ................ 382/149 |
| 6,067,153 A | * | 5/2000 | Mizuno .................... 356/237.2 |
| 6,222,935 B1 | * | 4/2001 | Okamoto .................... 382/149 |
| 6,333,992 B1 | * | 12/2001 | Yamamura et al. ......... 382/149 |
| 6,476,388 B1 | * | 11/2002 | Nakagaki et al. ........... 250/310 |
| 6,567,168 B2 | * | 5/2003 | Nara et al. .................. 356/394 |

FOREIGN PATENT DOCUMENTS

| | | |
|---|---|---|
| JP | 09280845 | * 10/1997 |
| JP | 2000-067243 | 3/2000 |
| JP | 2000-195458 | 7/2000 |

* cited by examiner

Primary Examiner—Hou Q. Pharma
Assistant Examiner—Sang H. Nguyen
(74) Attorney, Agent, or Firm—Townsend and Townsend and Crew LLP

(57) ABSTRACT

A method to solve the problem of a technique generally used to detect a defect of a semiconductor by calculating the differential image based on pattern matching, which requires that a reference image must be picked up to pick up an image of the inspection position in an area with the semiconductor pattern having no periodicity, resulting in a low throughput. The image of the inspection position is divided into local areas, each local area is matched with the local area of the image already stored and the difference between the local areas thus matched is determined to extract area.

18 Claims, 7 Drawing Sheets

SEQUENCE PARENT PROCESS

SEQUENCE CHILD PROCESS
FOR DEFECT EXTRACTION

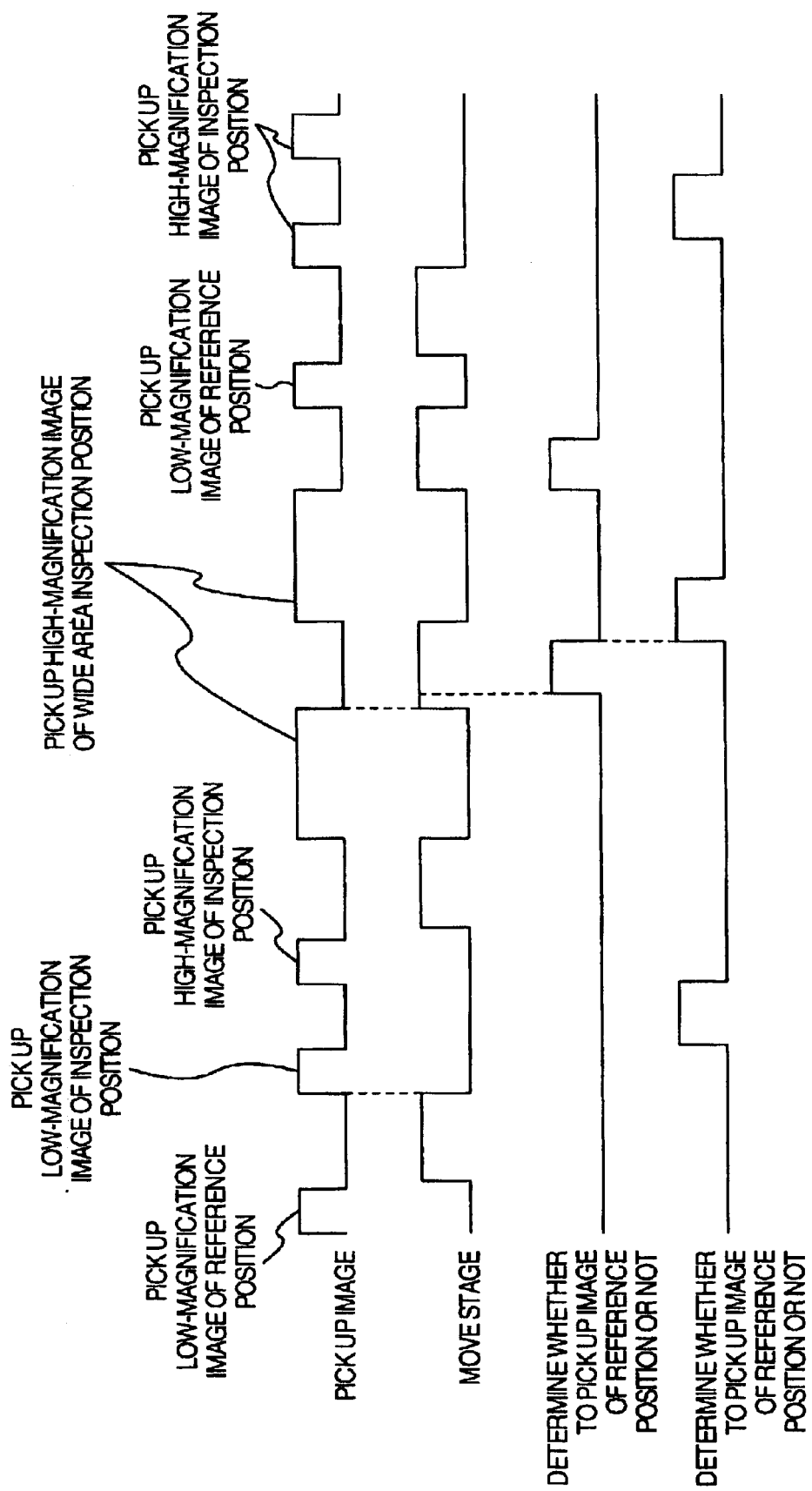

601

603

602

604

701

702

METHOD OF REVIEWING DETECTED DEFECTS

BACKGROUND OF THE INVENTION

The present invention relates to a method of inspecting the external appearance and reviewing defects of a semiconductor, or in particular to a technique for increasing the speed of an apparatus for reviewing defects of a semiconductor.

The conventional method of inspecting and reviewing defects of a semiconductor generally employs a comparative inspection in which the image of an inspected portion is compared with the image of the corresponding portion of a conforming article, and the difference between them is extracted as a defect. The method in which the images of the external appearance of the portions of the same design of different chips in the same wafer are compared for inspection is called a chip comparison method, while the method in which the images of the external appearance of the portions designed to have the same external appearance in the same chip are compared for inspection utilizing the characteristics of the areas having a periodic pattern such as a memory cell is called a cell comparison method. In the inspection areas adapted for the cell comparison, the semiconductor pattern can be considered to have a predictable periodic pattern. The first category of the cell comparison method is disclosed in JP-A-2000-67243, in which a single periodic pattern is stored in advance as a reference image and compared with a plurality of images of a plurality of inspected portions thereby to extract a defective area. In the second category of the cell comparison method, as disclosed in JP-A-2000-195458, a periodic pattern is divided into a plurality of rectangular areas, each of which is displaced by an integer multiple of the pattern period, and it is determined that a defect exists in a rectangular area associated with the maximum total sum of the differences.

The first category of the cell comparison method presupposes that the periodic pattern is identical at each position of the wafer. It is therefore difficult to successfully meet the situation where a plurality of different periodic patterns exist in a wafer. Also, with regard to the first category of the cell comparison method, in spite of the description about the mode for automatically determining whether the pattern at an inspection position is periodic or not, it is difficult to determine automatically only from an image whether a given pattern is periodic or not. Further, the process for automatic determination of a periodic pattern is accompanied by a great amount of calculations, and the first category of the method requires a waiting time before this determination process is completed. Furthermore, the second category of the method, which presupposes that the pattern at the inspection position is periodic, is not applicable in the case where the pattern periodicity is unknown.

SUMMARY OF THE INVENTION

An object of the present invention is to provide an apparatus for reviewing defects of a semiconductor which is capable of operating at high speed with a high throughput.

Another object of the invention is to provide a method of reviewing defects in which a reference position constituting a normal portion can be prevented from being contaminated by an electron beam in the case where the image pick-up means is a SEM (Scanning Electron Microscope).

Specifically, according to this invention, there is provided a method of reviewing defects, comprising:

the defect image pick-up step for moving the field of view of the microscope to a sample inspection position and picking up an image of the external appearance of the inspection position;

the reference image pick-up determination step for determining whether the image of the external appearance of a reference position designed to have the same external appearance as the inspection position is to be picked up or not;

the reference image pick-up step for moving the field of view of the microscope to the reference position and picking up an image of the external appearance of the reference position in accordance with the result of determination in the reference image pick-up determination step;

the defect area extraction step for extracting a defect area of the inspection position from selected one of the image of the external appearance alone of the inspection position and both the image of the external appearance of the inspection position and the image of the external appearance of the reference position in accordance with the result of determination in the reference image pick-up determination step; and the defect area post-extraction step for is executing a process based on the result of extraction of the defect area;

wherein the reference image pick-up determination step includes at least one of the image pick-up pre-start reference image pick-up determination step for provisionally determining, before the defect image pick-up step, whether to pick up the image of the external appearance of the reference position and the image pick-up post-start reference image pick-up determination step for finally determining, after the defect image pick-up step, whether to pick up the image of the external appearance of the reference position; and wherein the defect image pick-up step or the reference image pick-up step is executed concurrently with the image pick-up post-start reference image pick-up determination step, for a different inspection position than the inspection position determined in the image pick-up post-start reference image pick-up determination step.

These and other objects, features and advantages of the invention will be apparent from the following more particular description of preferred embodiments of the invention, as illustrated in the accompanying drawings.

BRIEF DESCRIPTION OF THE DRAWINGS

FIG. 3 is a timing chart for the sequence of operation according to the invention.

DESCRIPTION OF THE EMBODIMENTS

An embodiment of the invention will be explained with reference to FIGS. 1 to 8.

Figure 1:
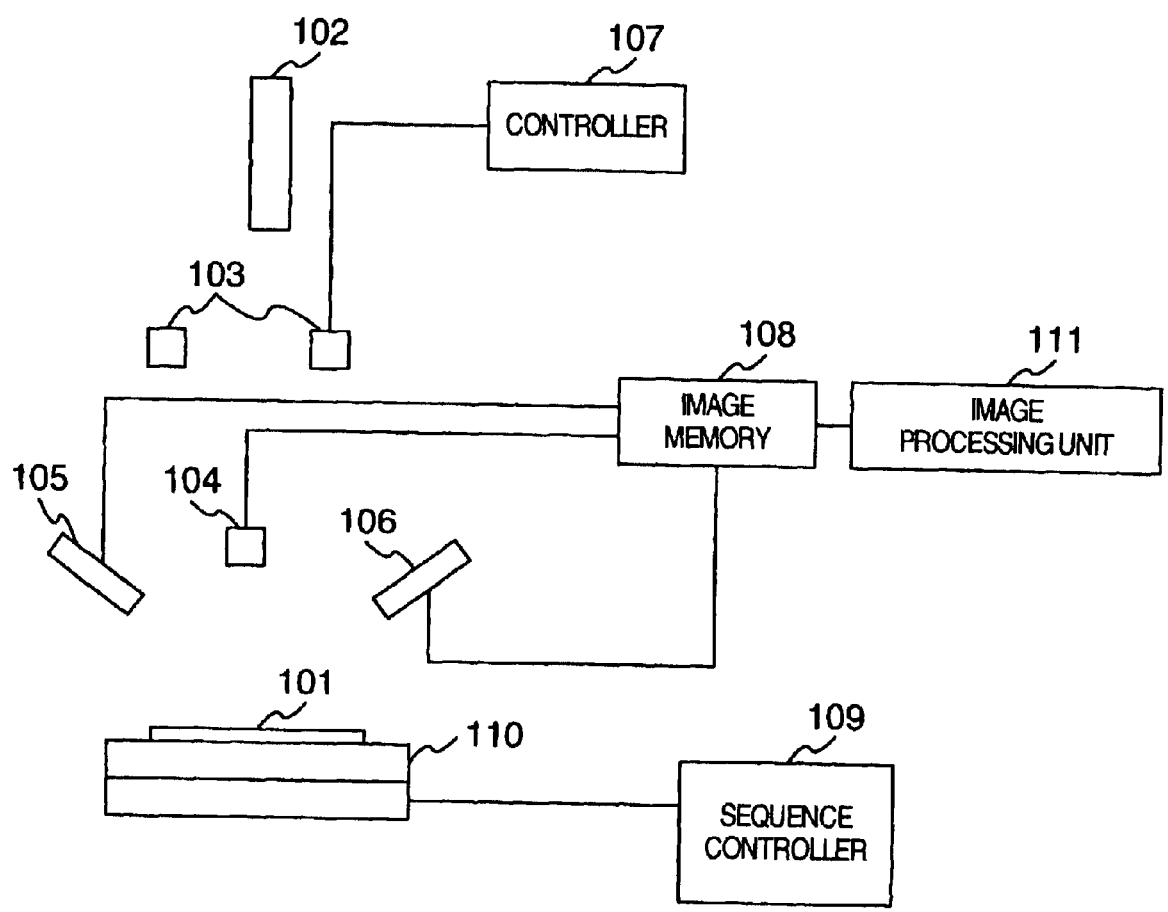
FIG. 1 is a front view showing a general configuration of a review system according to the invention.

FIG. 1 is a diagram showing a general configuration of a review system for analyzing a defect generated in a semiconductor wafer according to an embodiment of the invention. Reference numeral 101 designates a sample to be inspected which is mounted on an XY stage 110. Numeral 102 designates an electron gun for radiating electrons on the sample 101 through electron scanning units 103. An image pick-up unit 104 is secondary electron detection means. Numerals 105, 106 designate narrow-angle electron detector for detecting electrons from a given narrow angle. The narrow-angle electron detectors 105, 106 are arranged in different directions for detecting electrons at narrow angles. The electron scanning units 103 are controlled by a control unit 107 for two-dimensionally scanning the electrons emitted from the electron gun 102.

Numeral 108 designates an image memory for storing the outputs of the electron detectors 104, 105, 106. Electrons are two-dimensionally scanned and radiated by the electron scanning units 103, and therefore an image having a different characteristic for each detector is stored in the image memory 108. In image processing unit 111, the images stored in the image memory 108 are processed and a defect is extracted. An image of the defect thus extracted is displayed on a display screen. The narrow-angle electron detectors 105, 106 can produce an output which is stronger, the smaller the angle between the direction of each detector and the normal to the sample 101. By use of this characteristic, for example, the slope of the sample can be detected. Thus, a three-dimensional shape can be estimated, for example, as disclosed in JP-A-60-249008.

Numeral 109 designates sequence controller capable of moving the inspection view of field by controlling the XY stage. In collaboration with the controller 107, the sequence controller 109 controls the entire sequence of the operation of the system for reviewing a plurality of inspection points in a semiconductor defect. A defect extraction method using this configuration is disclosed, for example, in Japanese Patent Application No. 2001-217510 filed earlier by the present inventors, in which an image of an inspection position is compared with an image of a reference position corresponding to the inspection position thereby to extract a defect.

The patterns that the sample is to have at the inspection position and the reference position are required to coincide with each other. As described in JP-A-2000-67243, therefore, a technique for extracting a defect utilizing the periodicity of the pattern of the inspection positions is generally known, in which the periodic pattern imaged in advance is compared with the image picked up at each inspection position, by switching between the mode requiring no process of picking up an image of a reference position for each inspection position and the mode for picking an image of a reference position representing a corresponding coordinate position in an adjoining chip for each inspection position. This technique has the function of automatically determining whether a repetitive pattern is involved in the case where it is not determined in advance whether the image of a reference position is not required to be picked up. This function, however, is accompanied by the problem of a reduced throughput and the difficulty of stable automatic determination. Further, due to the inapplicability to other than a repetitive pattern, the technique cannot be used for the system LSI or the like which has recently come to be mass-manufactured. The reduced throughput will be explained first.

A semiconductor review system generally requires that the stage is moved to the defect position detected by an automatic wafer inspection device and, after more accurately determining the defect position at a low magnification, the image of the defect position is picked up at a high magnification. In an application of the method described in JP-A-2000-67243, however, as shown in FIG. 2 thereof, it is required to determine whether a repetitive pattern is involved or not based on the image of the inspection position, and unless a repetitive pattern is not involved, to move the stage to the reference position and extract a defect position by picking up an image thereof. After this, the stage is moved to the defect position again and an image of the defect position is picked up with the defect located at the center thereof.

In the mode of picking up an image of a reference position for each inspection position, the image is picked up at the reference position with a low magnification, and then at the inspection position with a low magnification. After detecting a defect position using the two images of low magnification, an image at and around the detected defect position is picked up with a high magnification by controlling the electron scanning units 103. In the mode of automatically determining whether a repetitive pattern is involved or not, the stage is required to be moved one more time than otherwise, and also the processing time for automatically determining whether a repetitive pattern is involved or not is required. In the case where it is found that a repetitive pattern is not involved, therefore, the time cost is so high that the throughput cannot be improved.

This invention proposes a method of solving this problem. According to this invention, in order to eliminate the need of moving the field of view to the inspection position again after moving it to the reference position in the case where a repetitive pattern is not found to be involved, an image of the inspection position is picked up with a large field of view at high magnification, which is accompanied by an frame integration. Generally, in the case where an image is picked up using the electron microscope, the frame integration is carried out in order to improve the S/N ratio. In the frame integration, electrons are scanned on the inspection field of view a plurality of times, and the electrons detected by each scan are added up. The frame integration, if carried out a great number of times, requires a long image pick-up time, especially for a large field of view and a high magnification. Generally, therefore, it is actually disadvantageous to extract a defective area by comparing images with a large field of view at high magnification. The image pick-up time can be shortened by increasing the number of times the frame integration is carried out for picking up an image of the inspection position while reducing the number of times the frame integration is carried out for picking up an image of the reference position.

The S/N ratio of the image picked up at the reference position where the frame integration is carried out a fewer number of times is very low. Nevertheless, an image equivalent to a low-magnification image having a greater number of frame integrations can be obtained by subjecting the image and a low-pass filter to the convolution operation with down sampling. Comparison of images with different numbers of frame integrations shows different effects of the charging on the image. Thus, an image having the same number of frame integrations as at the reference position is required at the inspection position. Therefore, two images are generated at the inspection position, one associated with a time point during the frame integration process when the number of frames integrated becomes equal to that integrated for the image picked up at the reference position, and the other associated with a time point after the frame integrations are carried out the number of times required to obtain the final image quality. The effects of this method will be explained on the assumption that the image pick-up time per frame is 20 ms, the number of frame integrations is 12, the stage is moved for one second, the ratio of high to low magnification is 2.5, the time required for gain adjustment and auto focusing before picking up an image is 300 ms, the time required for automatic determination of a repetitive pattern is 500 ms and the time required for defect position extraction is 800 ms.

Figure 2A:
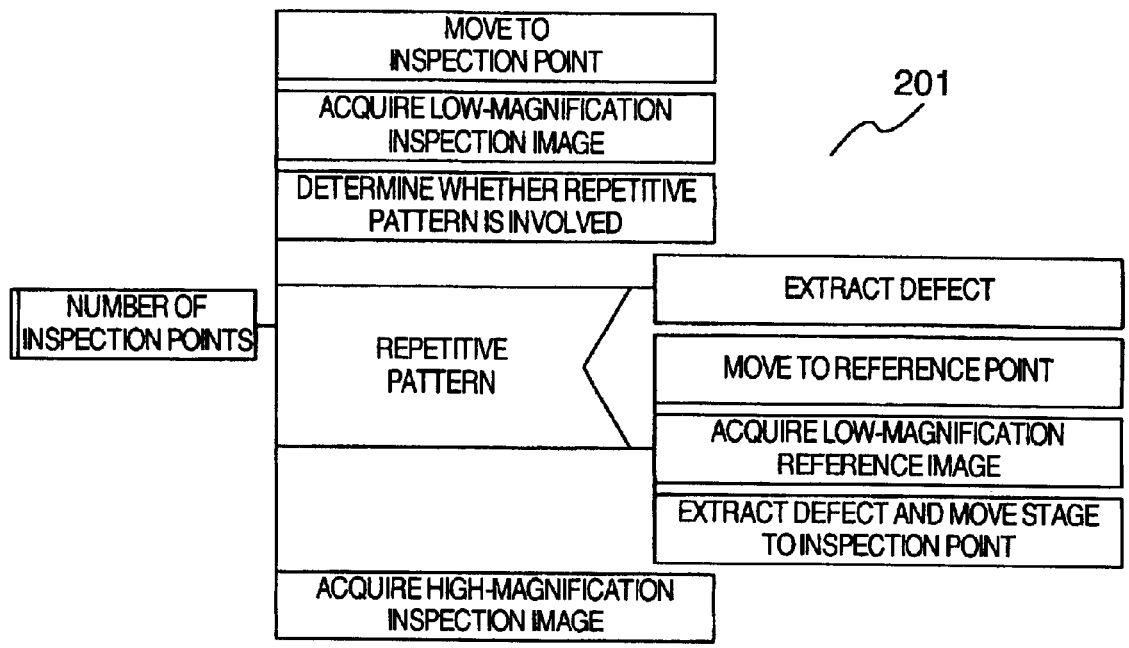
FIGS. 2A to 2D are sequence charts for explaining the flow of image comparison according to the invention.

Flowcharts used for comparison are shown in FIGS. 2A to 2D. In FIG. 2A, numeral 201 represents a more strict version of the flow description in JP-A-2000-67243. The time required for picking up a defect image at low magnification is 540 ms including the pre-processing, and the subsequent process for automatic determination of a repetitive pattern requires 500 ms. In the absence of a repetitive pattern, on the other hand, it takes 1540 ms to move the stage to the image pick-up field of view of a low-magnification reference image at the reference image position. Then, it takes 1 second to move the field of view to the defect position by moving the stage while at the same time extracting a defect. Finally, the image of the defect position is picked up at high magnification. The total time required is 4.1 seconds. With the additional time required to move the stage to such an extent that the inspection position is first covered by the image pick-up field of view, the total time adds up to about 5.1 seconds. In the case where a repetitive pattern is found to be involved, on the other hand, the image at the reference position is not needed and therefore the total time is reduced from 5.1 seconds to 3.4 seconds.

Figure 2B:
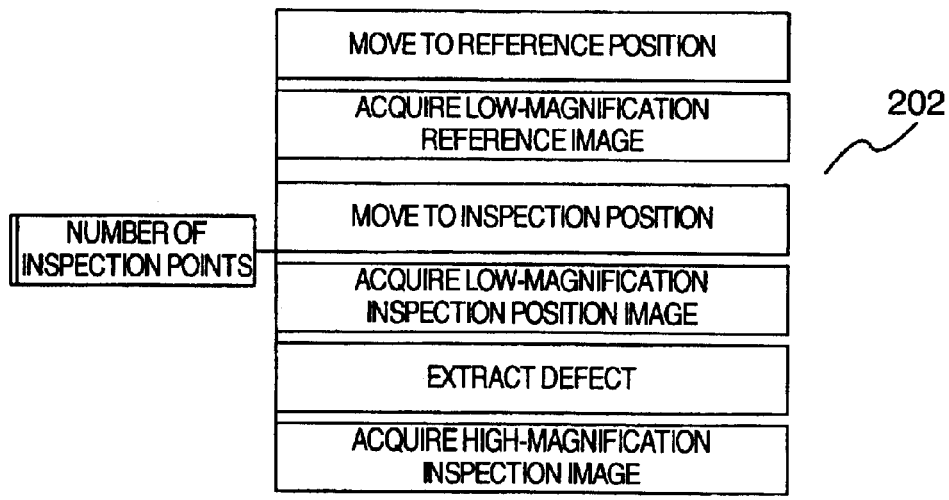

In the mode 202 shown in FIG. 2B in which the automatic determination of a repetitive pattern is not carried out, in contrast, 540 ms is required for picking up an image of the reference position, one second for moving the stage, 540 ms for picking up an image at low magnification, 800 ms for extracting a defect, and 540 ms for picking up an image of a defect position at high magnification, for a total of 3.4 seconds. This adds up to 4.4 seconds when including the time first required for moving the field of view to the reference position. It is thus understood that the method 201 is about one second speedier in the presence of a repetitive pattern, and about one second slower in the absence of a repetitive pattern. All these facts indicate that the throughput is reduced unless a repetitive pattern appears with the probability of not lower than 50%.

Figure 2C:
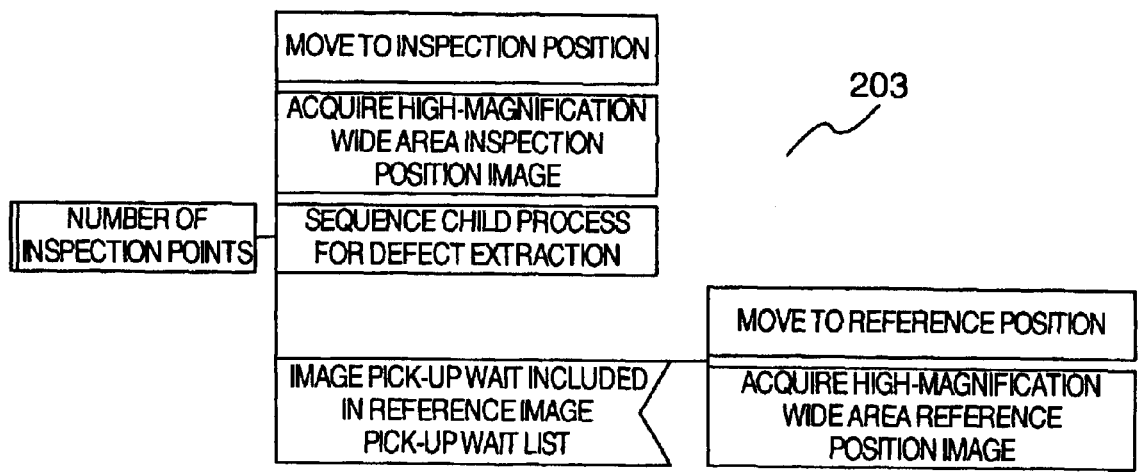
Figure 2D:
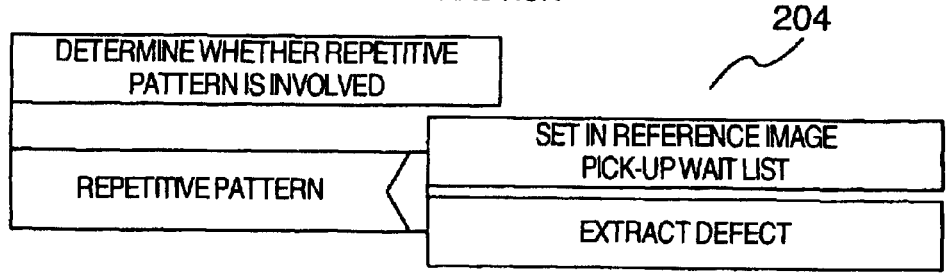

In the sequential processes 203 and 204 shown in FIGS. 2C and 2D, respectively, according to the invention, an image at the inspection position is picked up in a wide field of view with a high resolution, thereby eliminating the sequence for picking up an image after defect extraction for a high-magnification image at the inspection position. In this way, the increase in the review time can be minimized in the case where the image at the inspection position has no repetitive pattern. As an image having an extracted defect, a high-magnification image picked up at the inspection position in a wide field of view with a high resolution is displayed on the screen. The image of the defect thus extracted can also be displayed on the screen also after automatic classification.

In view of the fact that an image of high resolution is picked up in a wide field of view, however, a longer image pick-up time of 1800 ms is required than in the process 202 for picking up an image at the inspection position. In the case where the image of the reference position is not picked up, the processing time is 2800 ms including the time required for moving the stage to such an extent that the inspection position is covered by the field of view. Since the high-magnification image is already acquired, the sequential determination of the necessity to pick up an image at the reference position is not required, but can be carried out concurrently with the subsequent stage movement to the inspection position or the image pick-up process.

In the case where the processing with a single image is impossible and an image is required to be picked up at the reference position, the additional time is required for moving the field of view to the reference position and picking up an image at the reference position. The performance substantially equal to that of defect extraction from the image at the low-magnification inspection position and the reference position in the process 201 or 202 can be achieved by processing the image subjected to the down sampling for reducing the size of the image picked up with high resolution to 1/2.5 and extracting a defect. The down sampling includes the process of thinning a target image processed through a low-pass filter. The down sampling of 1/2.5, therefore, can improve the S/N ratio with the same effect as in 6.5 sessions of frame integration.

In the processes 201 and 202, frames are added 12 times while picking up a low-magnification image. The processes 203 and 204, on the other hand, can improve the S/N ratio due to the same effect as if the frame integration has already been carried out 6.5 times. At the reference position, therefore, an equivalent S/N ratio can be achieved once an image is picked up with two frame integrations. In this case, the image pick-up time is 560 ms including the pre-processing or 1560 ms including the stage movement. Thus, the total time is 4.4 seconds. Specifically, it is understood that in the case where the image of the reference position is required to be picked up, the processing time can be shortened more than in the process 202 having a higher throughput than the process 201. Also, it is understood that in the case where the image of the reference position is not required to be picked up, a throughput higher than that of the process 201 which is higher than in the process 202. Assume that the frame integration is carried out at the reference position the same way as at the inspection position for picking up an image. In the case where an image at the reference position is required to be picked up, the time as long as 6.6 seconds is required in all; resulting in the lowest throughput of all.

In the method according to this invention, the high image pick-up magnification at the defect position is effective up to about three times the low magnification. In the case where this limit is exceeded, however, the throughput would be reduced especially when the image at the reference position is required to be picked up. In the case where it can be determined before picking up an image at the inspection position that the possibility of extracting a defect is high only with the image at the inspection position, it is desirable that the sequence according to the invention including the process 201 or 203 combined with the process 204 is employed, while the process 202 is employed in the case where the such possibility is low. The possibility of processing only with the image at the inspection position beforehand can be determined, for example, based on the method employed when each inspection position is inspected using another inspection system.

Generally, the semiconductor is inspected by either of two methods. One is a chip comparison inspection in which the external appearances at the same coordinate position of adjoining chips are compared with each other. The other is a cell comparison inspection in which the pattern periodicity in each chip is utilized. It is known that in the case where a defect is inspected by the cell comparison method, the inspection positions represents a periodic pattern. As a result, a higher throughput is expected when using the sequence 201 for executing the process according to the invention shown. With regard to the chip comparison method, on the other hand, the process using the sequence 202 is expected to produce a higher throughput for a high image pick-up magnification.

A timing chart according to the invention combined with the process 202 is shown in FIG. 3. The periodicity cannot sometimes be determined based on the method of inspecting each inspection position using another inspection device. In such a case, the possibility of defect extraction can be determined, based on the image of the inspection position alone, by using the design data of the inspection position. Assume that an image of a reference position corresponding to a position different from the inspection position involved is picked up as a reference image. The design data for each position is registered generally as a stroke data. Based on this stroke data, the wiring pattern in the field of view at the reference position is stored as image data.

Next, the wiring pattern in the field of view corresponding to the inspection position involved is converted into image data from the stroke data. The two imaged design data are compared with each other using the pattern comparison method, and in the case where the patterns are coincident, it is determined that a defect can be detected from the image of the inspection position by using the image of the reference position corresponding to the different position as a reference image. Also, in extracting a defect using only the periodicity of the pattern at the image pick-up position without using the image at a different inspection position as a reference image, it is similarly possible to determine using the design data whether a defect can be extracted only from the image at the inspection position. Specifically, the wiring pattern in the field of view at the inspection position is converted into image data from the wiring pattern registered as stroke data, and using the auto-correlation, it is determined whether the same pattern appears at different positions in the field of view at the inspection position.

The necessity of picking up an image of the reference position corresponding to the inspection field of view involved is not always accurately determined before picking up the image. As described previously, in many cases where the image appearing in the field of view can be predicted based on the design data, the possibility of cell comparison can be determined before picking up an image of a defect. In the actual production line, however, the design data cannot be always acquired. After picking up an image, therefore, it is necessary to determine, using the image picked up, whether the image at the reference position corresponding to the inspection position is required to be picked up or not.

One method for this determination is consists in determining the periodicity of the pattern imaged based on the image of the defect position, for example, and determining that the defect cannot be extracted, using the periodicity of the pattern within the image picked up at the inspection position in the case where the inspection field of view is small as compared with the pattern periodicity. In the case where the defect size is larger than the pattern periodicity, on the other hand, defects are undesirably compared with each other, and therefore it becomes difficult to detect the defective area accurately. Especially in the case where the automatic classification or the size determination of a defect becomes necessary, a better performance could be expected by determining that the defect cannot be extracted.

The foregoing description of the method of extracting a defect from an image at the defect position presupposes the cell comparison and the comparison of the reference image. With the logic LSI or the like, however, neither of the aforementioned two methods is applicable to a greater proportion of images at the defect position. The cell comparison is not applicable in the case where the pattern has no periodicity in the field of view. The reference image comparison, on the other hand, cannot be used unless the reference image is coincident with the image in the field of view. This is because the pattern of the logic LSI or the like is complicated. An effective method of detecting a greater number of defects without picking up an image of the reference position consists in matching each local area but not the whole of an image picked up at the inspection position involved.

Figure 4:
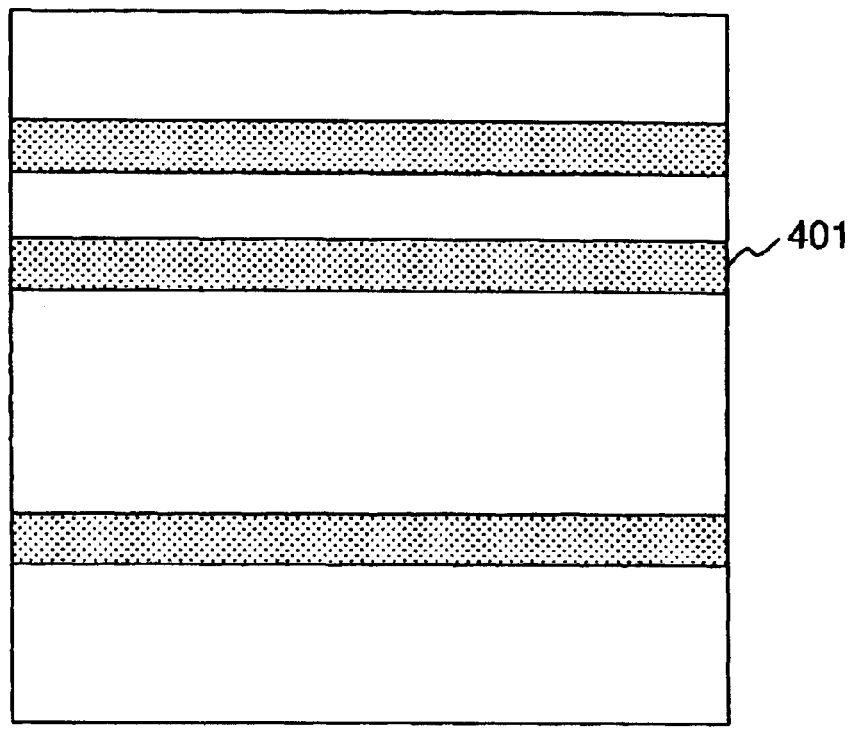
FIG. 4 is an image picked up from a wiring pattern.

First, a method of generating a reference image from the image picked up at the inspection position will be explained with reference to FIG. 4. Numeral 401 designates an image picked up at the inspection position including a wiring pattern. The wiring pattern, though not periodic, is configured of wires having substantially the same external appearance horizontally. Generally, a wiring pattern, which is an artificial object, has the same external appearance locally, although the defects can be assumed not to have the same external appearance. In the image at the inspection position, therefore, the same local area patterns are matched sequentially, and the best match of patterns, e.g. the patterns having the highest correlationship are compared with each other thereby to generate a differential image. A defect is thus determined based on the largest image pixel of the differential image, or it is determined that an area that has failed in matching is a defect.

Generally, the matching of local areas is accompanied by an increased amount of arithmetic operation. The use of pyramid matching or the like, however, can reduce the amount of arithmetic operation. Nevertheless, this method harbors the problem of difficulty to apply to the case where defects are generated over a wide area. The problem in application is how to set the local area size.

Figure 5:
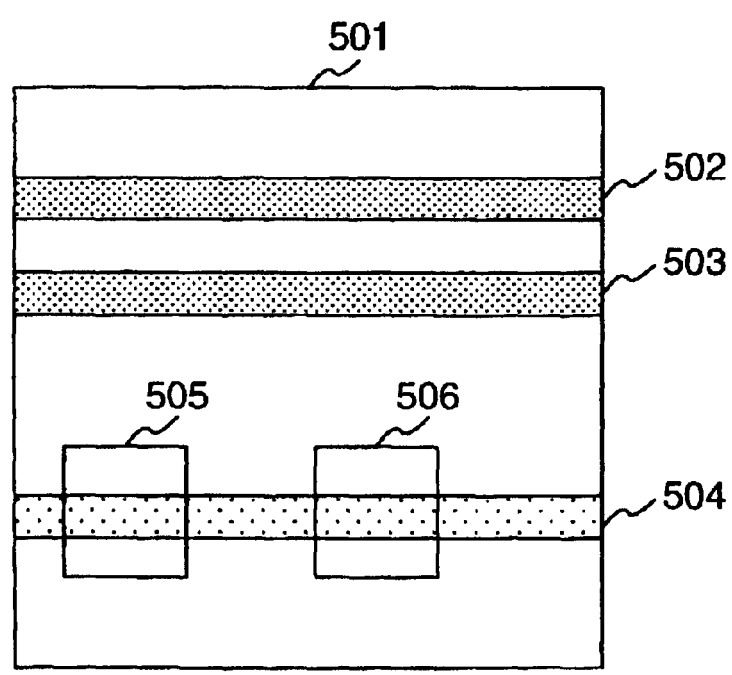
FIG. 5 is a diagram showing an image picked up from a wiring pattern and rectangular areas.

This point will be explained with reference to FIG. 5. Numeral 501 designates a secondary electron image picked up at the inspection position, including images of wires 502, 503, 504. Numeral 504 designates a defect of which the image picked up is brighter than the wires 502, 503. In the case where a detection system as shown in FIG. 1 is used for picking up an image, the wiring may be brightened in the case where a shorting occurs at any part of the wiring. This is called a potential contrast. In the case where the local area is set to a rectangle as indicated by numeral 505, the areas 506 and 505 constitute entirely the same pattern, thereby making it impossible to detect them as a defect.

This problem is solved not by matching the local areas in an image picked up at the defect position but by matching them with a local area of an image determined as a conforming article registered as a reference image. In the process, it is more desirable not to presuppose that all the local areas are rectangles of the same size. This is for reason of the fact that in the case where an area to be matched lacks a feature such as an edge, accurate evaluation of the matching is difficult. In the case where every area is set as a wide are not to cause the aforementioned phenomenon, in contrast, a plurality of wires are contained in the area, undesirably resulting in the determination that the area cannot be matched.

In the area that cannot be matched, the determination of a defect is impossible. This phenomenon can be effectively prevented by making sure that two or more wiring sets are not included in each local area. In the case where an arbitrary size of a local area is permitted, however, the amount of arithmetic operation increases vastly. In view of this, the matching is performed with comparatively small rectangular areas, and each local area is configured by combining such rectangular areas.

Figure 6A:
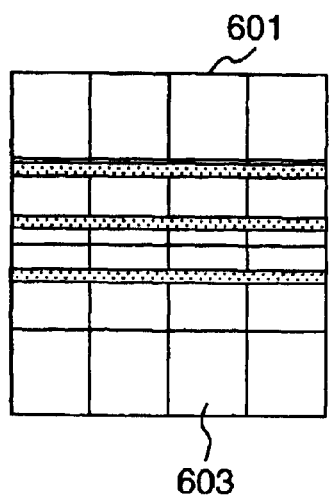
FIGS. 6A to 6C are diagrams showing an inspected image and a stored image.
Figure 6B:
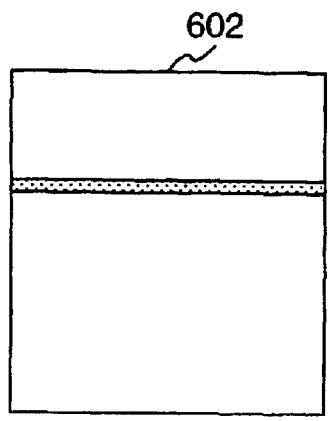

An explanation will be given with reference to FIGS. 6A to 6C. In FIG. 6A, numeral 601 designates an image picked up at the inspection position. In FIG. 6B, numeral 602 designates a reference image already picked up and registered. In the case where the local areas are formed of square areas of the same size as in the image 601, the areas corresponding to those indicated by numeral 603 are absent in the reference image 602, and therefore corresponding local areas for matching cannot be set in the reference image 602. This is attributable to the fact that the local area image 603 includes two wires.

Generally, the thickness and the edge appearance of the wiring in the same process are imaged in the same manner. The relative positions of different wires, however, are often different depending on the place where the images thereof are picked up. Especially, the two wires imaged in the local area 603 are distant from each other. The minimum distance between wires is determined by a particular process. In a semiconductor process for which as many wires as possible are required to be formed in a small area with a small distance between the wires, many local areas exist in which matching is possible within a reference image even in the case where a plurality of wires belong to one local area. In such a case, the image of the inspection position is divided in such a manner that wires having a long mutual distance belong to different local areas. The approximate wiring position can be determined by extracting an edge thereof from the image at the inspection position.

Figure 6C:
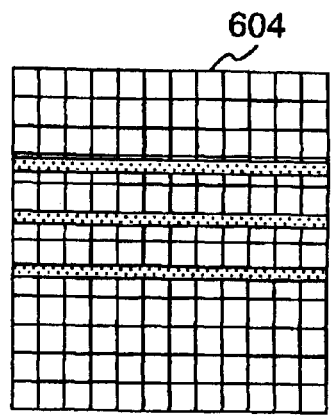
Figure 7:
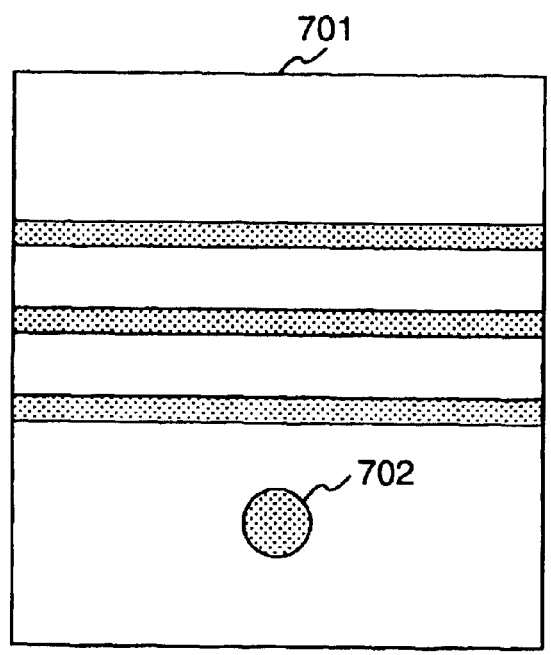
FIG. 7 is a diagram showing an inspected image.

The image at the inspection position is divided into comparatively small square areas as indicated by numeral 604 in FIG. 6C, and sampling points are set on the edges to secure as constant an interval as possible. An identifier of each corresponding square area is determined. Next, considering the sampling points on the edge at an interval wider than the previous sampling interval on the edge, and sampling points are set in areas free of an edge in such a manner as to secure as constant an interval as possible. An identifier of each corresponding square area is determined. Each square area corresponding to a sampling point on the determined edge or in an area free of the edge is regarded as a nucleus of a different local area. In the subsequent process, each area is expanded to such a degree that every square area included in the image 604 belongs to a local area. The areas which have come into contact with each other in the process are combined with each other. With regard to the sampling points on an edge, the expansion speed is increased in a direction in which edges are connected, and decreased in a direction in which they are not connected. In this way, a plurality of different wires can be prevented from belonging to the same local area.

Using this method, a local area having a plurality of different wires is not easily generated, and there are fewer cases in which a plurality of images are required to be matched as a local structure. Thus, the possibility becomes high of extracting a defect without an image at the reference position. By matching the image of the inspection position with a plurality of reference images, on the other hand, the accuracy of extraction without the image at the reference position is improved. Further, the image pattern of a local area corresponding to the image at an inspection position as well as a reference image can be effectively compared with a local area image at other positions in the image at the particular inspection position. In the case where a local area of the image at the inspection position is compared with a local area of the same image, a defect may be overlooked due to the potential contrast described above as an example. This problem can be avoided, however, by first comparing the local areas of the same defect position, and no defect being found there, by comparing the local area image determined from the reference image.

The method described above, however, harbors the problem that the reliability of defect extraction is low for the local area where matching fails and that a defect expanding to a large area may be overlooked. Assume that an image at the inspection position having an external appearance as indicated by numeral 701 in FIG. 7 has been picked up. No other portion having the same external appearance as the portion 702 is found in the area 701. In the case where a semiconductor pattern identical to the pattern 702 is not common, the reference image has a smaller chance of having a portion of the same external appearance as 702. As a result, the portion 702 is liable to be extracted as a defect in spite of its normalcy.

This problem can be solved by use of design data. The corresponding local areas should have the same design data, respectively. Thus, the local areas having the same design data are compared with each other. The design data generally indicate only the wiring or the hole positions, and often no data is available for the base wiring or the detailed shape of the wiring. Therefore, the image within a local area as well as the design data should be used for a decision. A defect is determined in the case where the same image of the local areas is not available in spite of the fact that the same design data provides reference data having a sufficient number of samples or the image of the inspection position. In the case where there is no local area having the same design data as the local area in the image of the inspection position, in contrast, a defect should not be determined even if the image of the same local area is not found. The design data of the wiring is generally configured of stroke data. The pattern matching between stroke data requires a smaller amount of calculations than the matching between images. Thus, first, the design data are compared with each other, and then the images in the local areas determined as identical are compared with each other.

Figure 8:
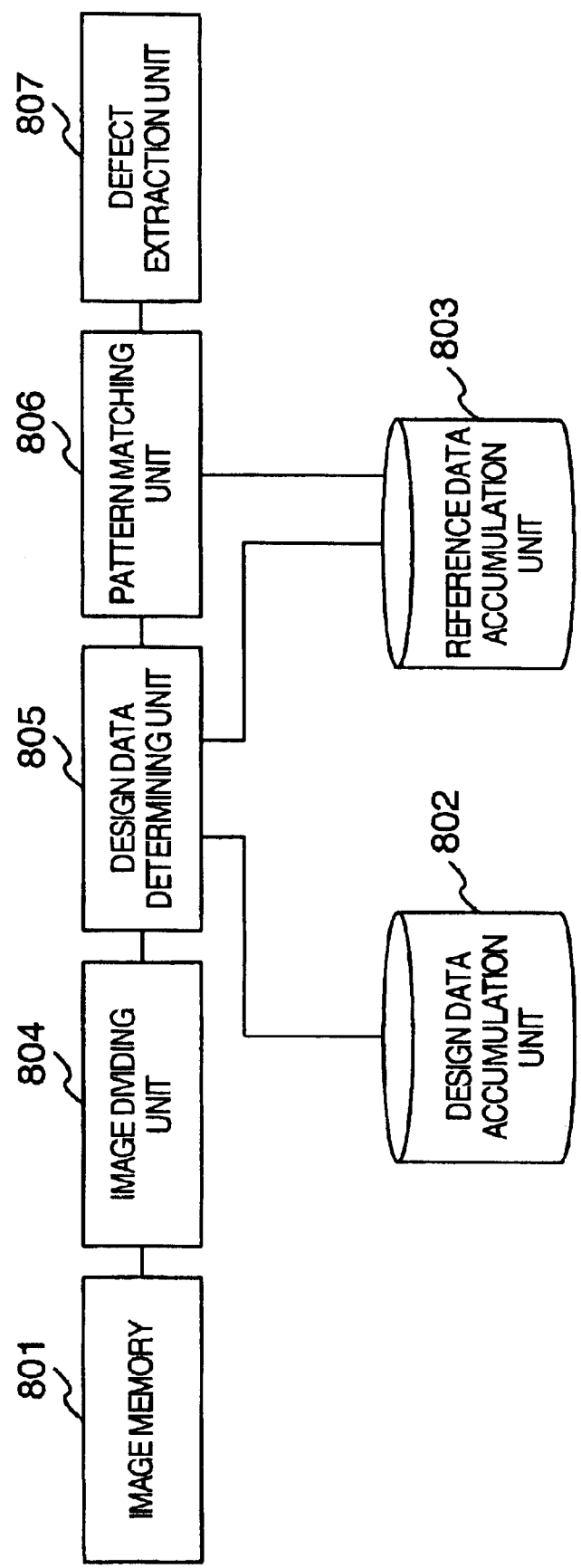
FIG. 8 is a block diagram showing a general configuration of a system for carrying out the review sequence using the design data according to the invention.

An example configuration is shown in FIG. 8. Numeral 801 designates an image memory corresponding to the memory 108 in FIG. 1. Numeral 802 designates design data accumulation unit for storing the design data for the field of view at the inspection position detected by the system shown in FIG. 1. Numeral 803 designates reference data accumulation unit for storing the design data and the image data of an image used as a reference image. The data can be accumulated in the reference data accumulation unit 803 before starting the review sequence for a group of inspection points. Nevertheless, the images picked up at the reference position in the review sequence can be sequentially accumulated.

Numeral 804 designates image dividing unit for dividing the image accumulated in the image memory 801 into a grid of squares, followed by dividing them into local areas using the method described above. Numeral 805 designates design data determining unit. The design data corresponding to each local area generated by the image dividing unit 804 is extracted from the design data accumulation unit 802, and matched with the design data of the reference image stored in the reference data accumulation unit 803 for each stroke data. Numeral 806 designates pattern matching unit. With regard to the local area image determined by the image dividing unit 804 and the local area image associated with the reference image accumulated in the reference data accumulation unit 803, which are determined as the same design data previously by the design data determining unit 805, the pattern matching is carried out between the local area image generated by the image dividing unit 804 and the reference image accumulated in the reference data accumulation unit 803. In the pattern matching unit 806, the image is subjected to the subband analysis based on the spatial frequency.

The components of each spatial frequency subjected to subband analysis which are smaller than a preset threshold level are set to zero in value and can be ignored in pattern matching. Generally, the place having a wiring requires consideration of the phase of the wiring. There are a few local areas with the design data thereof determined as identical in the design data determining unit 805, thereby leading to a small amount of arithmetic operation for the pattern matching. With regard to the areas lacking the wiring, on the other hand, the resulting lack of limitation due to the wiring phase increases the number of local areas of the reference image with identical design data as compared with the areas having the wiring. In view of the fact that the spatial frequency of the areas lacking the wiring contains a fewer high-frequency components, however, the actual amount of arithmetic operation can be considerably reduced by the processing to set a weak subband component to zero.

The processing in the pattern matching unit 806 makes it possible to determine a local area of the reference image corresponding to each local area in the image picked up at the inspection position, thereby producing an image corresponding to the image picked up at the reference position. Numeral 807 designates a defect extraction unit for generating a differential image for an area determined to have an identical pattern and determining a pixel having a difference as a defect.

The configuration shown in FIG. 8 is such that the matching is carried out only for the reference image. The image at the inspection position can be processed with the same configuration, however, by considering also the image at the inspection position in the process executed by the the design data determining unit 805 and the pattern matching unit 806. Specifically, the design data determining unit 805 compares the design data of the image at the inspection position stored in the design data accumulation unit 802, so that the local areas with the design data at a predetermined distance or more from each other and having identical design data are identified as corresponding local areas. In the pattern matching unit 806, the images of the corresponding local areas determined as identical in the design data determining means 805 are subjected to pattern matching with each other in the same manner as the reference image thereby to determine the corresponding areas.

In the case where the local areas at different inspection positions are compared, defects of the same type are compared, sometimes resulting in the same local area image. Even in the case where the local area images and the design data corresponding to the local areas are identical, a defect may be determined. Since the reference image can be determined free of defect, on the other hand, the condition is always normal in the case where both the design data and the local area images are identical between the reference image and the local area image.

As described above, the corresponding local area obtained at the inspection position and the corresponding local area obtained in the reference image are different in reliability. A solution to this problem is a method in which a weighting factor is multiplied and the probability of normalcy is determined as a conditional probability. The design data is used as such a condition. Let $\omega$ be the design data at a local area, and $\Omega$ a mass of local areas having the same design data $\omega$. Also assume that x is the image of the local area associated with the mass. The conditional probability to be determined is given as $P(x|\omega)$. The probability distribution function of this conditional probability is calculated taking the probability associated with each normal local area into consideration.

Generally, the probability distribution function is simply a histogram normalized in the case where X and $\omega$ are both satisfied at the same time. According to this method, the weight of voting is changed with respect to the histogram, based on an image from which a particular local area is obtained. Assume, for example, that a is the probability that the local area image obtained from the image at the inspection position is normal and 1 is the probability that the local area image obtained from the reference image is normal. The local area obtained from the image at the inspection position is multiplied by a, and the local area from the reference image is multiplied by 1 thereby to calculate a histogram. This histogram is normalized to determine a conditional probability distribution function. This method is used to calculate the normal probability corresponding to each local area, and a defect is determined for a local area having a low occurrence probability value.

In the configuration shown in FIG. 8, the image at a reference position is generated for each local area based on the data of the reference image group accumulated in the reference data accumulation unit 803 without picking up an image at the reference position. In an application of the defect inspection and the review method according to the invention to a new wafer, it is necessary to make sure that the defect extraction is normally carried out by this technique. For this purpose, the image generated at the reference position is required to be indicated to the user to prompt him to set a parameter or change the defect inspection mode and the review mode. The system for carrying out the inspection and the review is required to have the function of displaying both a defect and a reference image generated, which are displayed concurrently or alternately with each other. Also, for utilizing this invention actually on a semiconductor production line, it is important to make sure that the aforementioned image is displayed on at least one of the parameter setting screens for sequence control, imaging control and defect detection to prompt the user to switch the mode or change the parameters.

It will thus be understood from the foregoing description that according to this invention, the operating speed is increased and the throughput improved for the system for reviewing semiconductor defects. Also, according to this invention, the image at the reference position is not required to be picked up in the case where the image pick-up means is a SEM (Scanning Electron Microscope), thereby leading to the advantage that the reference position making up a normal portion is prevented from being contaminated by the electron beam.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A method for reviewing a defect, comprising:

a defect image pick-up step for moving a field of view of a microscope to an inspection position on a sample based on information from an inspection tool that has detected a defect and picking up an image at said inspection position;

a reference image pick-up determination step for determining whether an image of a reference position designed to have the same appearance as said inspection position is to be picked up or not;

a reference image pick-up step for moving said field of view of the microscope to said reference position and picking up an image of said reference position in accordance with a determination result produced in said reference image pick-up determination step; and defect area extraction step for extracting a defect area at said inspection position from at least a selected one of just the image of said inspection position or both the image of said inspection position and the image said reference position in accordance with the determination result;

wherein said reference image pick-up determination step includes at least a selected one of an image pick-up pre-start reference image pick-up determination step for provisionally determining, before said defect image pick-up step, whether the image of said reference position is to be picked up or not or an image pick-up post-start reference image pick-up determination step for finally determining, after said defect image pick-up step, whether the image of said reference position is to be picked up or not.

2. A method of reviewing a defect according to claim 1, further comprising:

an enlarged defect image pick-up step for picking up an image of said defect area determined in said defect area extraction step with a magnification larger than in said defect image pick-up step, an enlarged reference image pick-up determination step for determining whether an enlarged reference image of an area having the same appearance as the area with the image thereof picked up in said enlarged defect image pick-up step is to be picked up with the same magnification as in said enlarged defect image pick-up step, and an enlarged reference image pick-up step for picking up said enlarged reference image based on the result of determination result;

wherein said enlarged reference image pick-up determination step includes at least selected one of the image pick-up pre-start enlarged reference image pick-up determination step for provisionally determining, before said enlarged defect image pick-up step, whether said enlarged reference image is to be picked up or not, or the image pick-up post-start enlarged reference image pick-up determination step for finally determining, after said enlarged defect image pick-up step, whether said enlarged reference image is to be picked up or not.

3. A method of reviewing the defect according to claim 2, wherein a selected one of said defect image pick-up step, said reference image pick-up step, said enlarged defect image pick-up step, or said enlarged reference image pick-up step is executed concurrently with a selected one of said image pick-up post-start reference image pick-up determination step or said image pick-up post-start enlarged reference image pickup determination step for an inspection position different from the inspection position.

4. A method of reviewing a defect according to claim 1, wherein the microscope in said defect image pick-up step and said reference image pick-up step is an electron microscope, wherein the microscope in said defect image pick-up step and said reference image pick-up step is an electron microscope, wherein an image is obtained by scanning electrons at least once in the image pick-up field of view at each of an inspection position and a reference position, wherein both a defect search image whose number of frame integrations is the same as that of said reference image pick-up step and a defect review image whose number of frame integrations is greater than that of said reference image pick-up step are produced in said defect image pick-up step, and wherein a defect is extracted in said reference image pick-up determination step by comparing the defect search image picked up in said defect image pick-up step with the image picked up in said reference image pick-up step.

5. A method of reviewing the defect according to claim 1, wherein said defect area extraction step further includes:

statistical amount map calculation step for calculating the statistical amount indicating the existence probability for selected one of each of the local areas and the pixels of the image of said inspection positon based on the image of said inspection position and the inspection data registered for extracting a defect area from said inspection position, and a defect area calculation step for extracting a defect area by comparing the image of said inspection position with selected one of the image of said reference position and said statistical amount calculated in said statistical amount map calculation step.

6. A method of reviewing a defect according to claim 1, wherein the determination is made based on at least a selected one of the inspection method for the inspection system used for inspection of said inspection position before said defect inspection review method, the design data of said inspection position or said reference image picked up to extract a defect of an object different from said inspection position.

7. A method of reviewing a defect comprising:

a defect image pick-up step for moving a field of view of a microscope to an inspection position on a sample based on information from an inspection tool that has detected a defect and picking up an image at said inspection position; and a defect area extraction step for extracting a defect area at said inspection position from the image of said inspection position or an image stored in a memory, wherein said defect area extraction step furthe includes:

a statistical amount map calculation step for calculating a statistical amount indicating the existence probability for selected one of each of the local areas and the pixels of the image of said inspection position based on the image of said inspection position or stored reference images for extracting a defect area from said inspection position in such a manner that statistical amounts in a local area or pixels are calculated from local area or pixels in the image of inspection position or stored reference images that are determined to have the same pattern each other; and a defect area calculation step for extracting a defect area by comparing the image of said inspection position with a selected one of the image of said reference position and said reference image is synthesized in said referemce image generating step.

8. A method of reviewing a defect according to claim 7 wherein said defect inspection review method makes it possible to display a reference image generated in said reference image generating step as ari image to the user, and makes it possible for the user to confirm the generation of said reference image.

9. A method of reviewing a defect according to claim 7 wherein said reference local area is set in said reference image generating step in such a manner that said pattern in said local area is subjected to subband decomposition, and each subband component is obtained by subband decomposition of selected one of the image of said inspection position and said stored reference image.

10. A method of reviewing a defect, comprising:
a defect image pick-up step for moving the field of view of a microscope to a sample inspection position and picking up images of said inspection position by scanning a focused electron beam;

a reference image pick-up step for moving said field of view of said microscope to a reference position and picking up an image of said reference position by scanning and focused electron beam; and a defect ara extraction for extracting a defect area of said inspection position using said image of said inspection position and said image of said reference position;

wherein said image of said reference position is picked up in such a manner that the number of times of scanning said focused electron beam to a reference position in said reference imae pick-up step is smaller than the number of times of scanning said focused electron beam to an inspection position in said defect image pick-up step.

11. A method of reviewing a defect according to claim 10, wherein said defect image pick-up produces both a defect search image whose number of frame integrations is the same as the fram integrations in said references image pick-up step and a defective review image whose number of frame integrations than the fram integrations in said reference image pick-up step wherein in the defect area extraction step, the defect area is calculated based on said defect search image and said image of said reference position.

12. A method of reviewing a defect comprising:
a defect image pick-up step for moving a field of view of a microscope to an inspection position on a sample based on information from an inspection tool that has detected a defect and picking up an image at said inspection position;

a reference image pick-up determination step for determining whether an image of a reference position designed to have the appearance as said inspection position is to be picked up or not;

a referene image pick-up step for moving said field of view of microscope to said reference position and picking up an image of said reference position in accordance with a determination result produced in said reference image pick-up determination step; and a defect area extraction step for extracting a defeat area in said inspection position from at least a selected one of just the image of said inspection position or both the image of said inspection position and the image said reference position in accordance with the determination result, wherein said reference image pick-up determination step is executed concurrently with said defect image pick-up step or said reference image pick-up step.

13. An apparatus for reviewing a defect detected by an inspection tool comprising:
a stage to hold a sample to be inspected, said stage configured for translation in X- and Y-direction to position said simple in said X- and Y-directions;

a scanning electron microscope to irradiate and scan a converged electron beam onto a sample that is held in said stage, and to detect electrons emanated from said sample by said electron beam;

an image memory to store of images of said sample;

an image processor to obtain said images and to process said images to produce a precise image of a defect on said sample, wherein an image of said sample is obtained by scanning an area of said sampl with said electron beam, detecting said electrons, and performing one or more frame integrations of detected electrons; and a controller to control positioning of said stage to perform scannin operations, wherein a defect detected on said sample by an inspection tool can be positioned within a viewing field of said scanning electron microscope to obtain an image of said sample referred to as a defect image, wherein a reference area on said sample can be positioned within the viewing field of said scanning electron microscope to obtain an image of said sample referred to as a reference image wherein the nunber of frame integration of said defect image is greater than the number of frame integration of said reference image.

14. The apparatus of claim 13 wherein said image processor is operable to process said reference image to have a quality metric substantially the same as that of an image obtained using the same number of frame integrations as used with said defect image.

15. An apparatus for reviewing a defect detected by an inspection tool comprising:
a stage to hold a sample on which a plurality of pattersn are formed and whcih are to be inspected, said stage being translatable in X- and Y-directions;

scanning electron microscope to irradiate and scan a converged electron beam onto a sample that is held in said stage, and to detect electrons emanated from said samply by said electron beam;

an image memory to stor an image of said sample;

an image processor to obtain said images and to process said images to produce a precise image of a defect on said sample, wherein said image of said sample is obtained by scanning an area of said sample with said electron beam, detecting said electrons, and a controller to control positioning of said stage to perform scanning operations, p1 wherein said defect area is calculated from a comparison of at least two local areas in said image, wherein said image processor is operable to form said local areas that are expected to have similar patterns.

16. The apparatus of claim 15 wherein said controller is operable to control said scanning electron microscope to produce an enlarged image of said defect.

17. A method for reviewing a defect, comprising:

moving a field of view of a microscope to an inspection position on sample based on information from an inspection tool that has detected a defect;

picking up an image at said inspection position;

a reference image pick-up determination step for determining whether an image or a reference position designed to have the same appearance as said inspection position is to be picked up or not;

a reference image generation step for generating a reference image; and a defect area calculation step for extraction a defect area by comparing the image of said inspection position with said reference image, wherein said reference image is generated according to said reference image pick- up determination step, either by moving said fielf of view of the microscope to said reference position and picking up an image of said reference position or from a partial image of said image of said inspection portion.

18. A method of reviewing a defect according to the claim 17, wherein said reference image pick-up determination step is executed concurrently with said picking up an image at said inspection position or reference image generation step.

* * * * *